United States Patent [19]
Van Scott et al.

[11] 4,194,007
[45] Mar. 18, 1980

[54] α-HYDROXYRETINOIC ACID, α-KETORETINOIC ACID AND MIXTURES AND THEIR USE IN TREATING SKIN CONDITIONS

[76] Inventors: Eugene J. Van Scott, 1138 Sewell La., Rydal, Pa. 19046; Ruey J. Yu, 4 Lindenwold Ave., Ambler, Pa. 19002

[21] Appl. No.: 869,351

[22] Filed: Jan. 13, 1978

[51] Int. Cl.$^2$ .......................... A61K 31/20; C11C 1/00
[52] U.S. Cl. ..................................... 424/318; 260/413
[58] Field of Search ................. 260/413; 424/317, 318

[56] References Cited

U.S. PATENT DOCUMENTS 3,920,835   11/1975   Van Scott et al. .................. 424/317

Primary Examiner—V. D. Turner
Attorney, Agent, or Firm—LeBlanc, Nolan, Shur & Nies

[57] ABSTRACT

Discloses α-hydroxyretinoic acid, α-ketoretinoic acid and mixtures thereof as well as compositions containing the same that are useful in the treatment of skin diseases, and particularly skin diseases exhibiting abnormal keratinization.

14 Claims, No Drawings

α-HYDROXYRETINOIC ACID, α-KETORETINOIC ACID AND MIXTURES AND THEIR USE IN TREATING SKIN CONDITIONS

This invention relates to α-hydroxy and α-ketoretinoic acids and to equilibrium mixtures containing the same all of which are hereinafter referred to collectively as α(hydroxyketo)retinoic acids. It also concerns therapeutic compositions containing α(hydroxy-keto)retinoic acids and the use of such compositions in the treatment of certain diseases usually characterized by a disturbance in epithelial keratinization. More particularly, it also concerns methods for the treatment of skin diseases in which disturbance of keratinization is a primary or secondary feature of the pathology.

Alpha-hydroxyretinoic acid and α-ketoretinoic acid are believed to be distinct chemical entities having formulas A and B respectively given below. However, they also are thought to exist in equilibrium as the keto-enol forms that can be illustrated as follows:

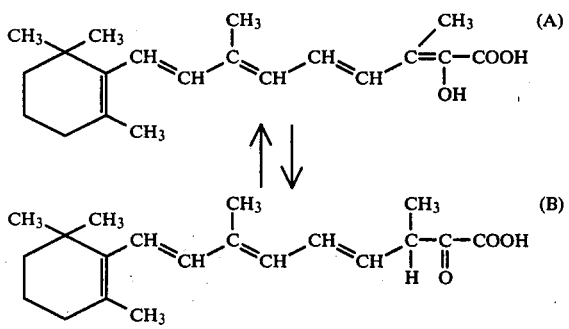

These compounds are related to retinoic acid which is also sometimes referred to as Vitamin A acid. The preparation of retinoic acid has been described in the literature (See U.S. Pat. No. 3,006,939 and Lakshmananet et al, Biochem. J. 90 569 (1964). It is also disclosed in the prior art as being useful as a keratolytic agent. (See Merck Index, 9th Edition, p. 1060).

A variety of skin conditions or disorders are known in the literature that involve some abnormality in the keratinization of epidermal epithelial tissue either as a primary factor or as secondary factors. Ordinary dry skin, for example, that is frequently an impairment of old age, although it appears to be associated with a deficient epidermal synthesis or retention of physiologic humectants also appears to be due to a relative incompetence of some aspects of keratinization. The heritable ichthyoses, as another example, are a group of genetically transmitted skin diseases that are also known to involve an abnormality in epidermal keratinization. In these cases, the pathology involved appears to be a hyperkeratinization that involves only the epidermal epithelium.

Other skin disorders that involve an abnormality in keratinization include such conditions as acne, dandruff, palmar and plantar hyperkeratosis, psoriasis, eczema, mycosis fungoides, Darier's disease, and lichen simplex chronicus. Any substance that promotes normal keratinization would have a tendency to have a beneficial effect in treating all of the above-mentioned conditions. It has now been found that α(hyroxy-keto)retinoic acids in therapeutically effective amounts are useful in promoting normal keratinization of epithelial tissue and particularly of the epidermis. Its action is thought to involve a control of the rate of keratinization but this may not be its exclusive action.

It has already been suggested in the prior art that epidermal keratinization as is experienced in ichthyosis may be controlled with certain α-hydroxy or α-keto acids. In this connection, see Van Scott and Yu, Archives of Dermatology, October 1974, Vol. 110, pages 586 to 590. However, nothing in this reference suggests that α(hydroxy-keto)retinoic acids, as described herein, would have a beneficial effect on normalizing epidermal keratinization.

Fed. Proc. 23, 294 (1964) and Nutrition Review, 24 113–116 (1966) suggests that K. Yagishita et al have isolated a hydroxylated metabolite of retinoic acid. However, there is no suggestion that this metabolite is the α(hydroxy-keto)retinoic acids of this invention.

In "The Vitamins" Second Edition, (1967), Vol. I, p. 46-47 edited by W. H. Sebrell Jr. and R. S. Harris, there is described the preparation of the hydroxy nitrile:

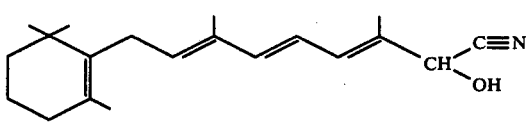

and the vitamin A acid nitrile:

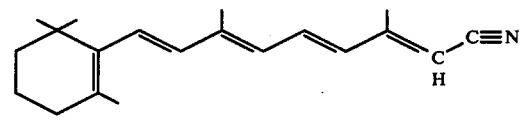

However, the α(hydroxy-keto)retinoic acids of this invention are not disclosed.

Arens et al in Nature, Vol. 157, (1946) p. 190-191 describe the synthesis of some compounds possessing vitamin A activity. These, however, are not the α(hydroxy-keto)retinoic acids of this invention.

Dowling et al, Proceeding of the National Academy of Sciences, Vol. 46, No. 5, May 15, 1960, p. 587–608 described in some detail the biological function of vitamin A acid. However, again there is no suggestion of the present invention in this reference.

Van Scott, in "Pharmacology and the Skin", p. 523-533 edited by W. Montagna, E. J. Van Scott and R. B. Stoughton describes a model for screening dermatological drugs. These include drugs intended for treatment of acne or psoriasis. There is, however, no suggestion for the use of the α(hydroxy-keto)retinoic acids described herein.

The two traditional ways of treating disorders in keratinization of the skin are by way of the use of hydrating agents or keratolytic agents. The former are intended to modify the stratum corneum to enhance its hydration. Typical agents useful for this purpose have been such things as water, glycerin, propylene glycol, etc. The keratolytic agents, on the other hand, are usually protein denaturants. These have the capability of disintegrating the stratum corneum to one degree or another, and solubilize one or more fractions which normally are insoluble. Typical agents of this type include urea.

The α(hydroxy-keto)retinoic acids employed in the present invention are believed to act not as a hydrating agent or keratolytic agent but as an agent that is a keratinization modifier i.e. that modifies the keratinization process. It may also function as a keratolytic agent but this is not its sole or even its most important mode of action.

Alpha(hydroxy-keto)retinoic acids may be made by the following synthetic scheme:

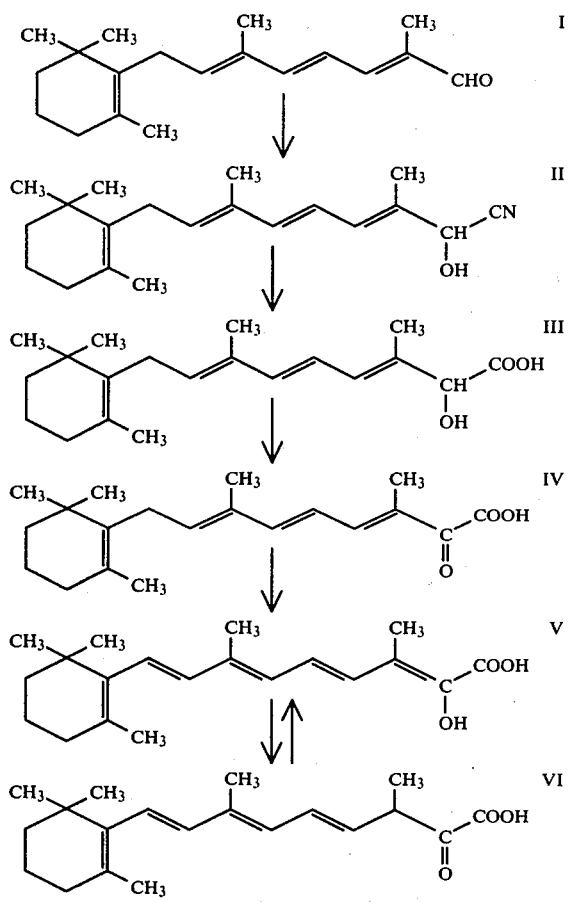

$C_{19}$ aldehyde (I) is a well known intermediate product employed in the chemical synthesis of retinoic acids as described by U. Schwieter and O. Isler (Chemistry of Vitamine A and Carotene in "The Vitamins", ed. by W. H. Sebrell, Jr. and R. S. Harris, p. 5-101, 1967).

When $C_{19}$ aldehyde (I) is reacted with acetone cyanohydrin a $C_{19}$ cyanohydrin (II) is formed as described by G. I. Samokhalov, L. P. Davydova, L. I. Zakharkin, I. M. Khorlina, L. A. Vakulova, L. T. Zhikhareva and N. Preobrazhenkii, J. Gen. Chem. USSR (English Trans.) 30, 1806 (1960). This $C_{19}$ cyanohydrin (II) may be hydrolyzed to α-hydroxy $C_{20}$ acid (III) according to a widely used method in the synthesis of α-hydroxy acids (C. A. Buehler and D. E. Pearson, Survey of Organic Synthesis, p. 752-753, 1970). The α-hydroxy $C_{20}$ acid (III) can be selectively oxidized to α-keto $C_{20}$ acid (IV) by a novel and specific oxidizing agent known as pyridinium chlorochromate which is commercially available. The method has been described in detail by E. J. Corey and J. W. Suggs, Tetrahedron Letter, 2647 (1975). The α-keto $C_{20}$ acid (IV) could be easily converted to the keto-enol mixture (V) by a well-known tautomerization in the presence of a common inorganic acid.

A slight variation in the method of synthesizing α-keto $C_{20}$ acid (IV) may be made by first esterifying α-hydroxy $C_{20}$ acid (III) to its methyl or ethyl ester. The α-hydroxy $C_{20}$ acid methyl or ethyl ester thus prepared is then oxidized with pyridinium chlorochromate as mentioned above. An α-keto $C_{20}$ ester thus synthesized may be readily hydrolyzed to α-keto $C_{20}$ acid (IV).

Alpha(hydroxy-keto)retinoic acids described herein should perform two physiologic functions; one as a α-hydroxy acid modulating keratinization, and the other as Vitamin A acid in modulating keratinization, modulating epithelial differentiation. Therefore, therapeutic compositions containing α(hydroxy-keto) retinoic acids as described in the following examples are to be useful in topical treatment of various skin disorders. As previously mentioned, these disorders would include disturbed keratinizations and inflammatory diseases such as dry skin, ichthyoses, dandruff, acne, keratoses, psoriasis, eczema, or mycosis fungoides.

Alpha(hydroxy-keto)retinoic acids described herein, like retinol, retinal or retinoic acid may have six representative steroisomers; namely, all-trans, 13-cis; 11-cis; 9-cis; 11,13-di-cis and 9,13-di-cis. The most stable and commonly used one, however, will be all-trans α(hydroxy-keto) retinoic acids which ordinarily will be used in the practice of the present invention.

The therapeutically effective concentrations of the α(hydroxy-keto)retinoic acids that may be contained in the compositions of the present invention may vary somewhat depending on the dosage form in which it is applied, the regimen and/or the mode of application. Generally, the concentration of α(hydroxy-keto)-retinoic acids may range from 0.01 to 2% by weight of the total composition. The preferred concentration range, however, is from 0.02 to 0.5% of the total composition.

In preparing the therapeutic composition of this invention, the α(hydroxy-keto)retinoic acids will ordinarily first be dissolved in a solvent, e.g. ethanol, acetone, isopropyl myristate, or mineral oil. The solution thus prepared may then be admixed in a conventional manner with any of the commonly available solution, gel, lotion, cream or ointment vehicles employed in the pharmaceutical arts.

The quantity of solvent employed (e.g. ethanol, acetone, isopropyl myristate, isopropyl palmitate, or mineral oil) to dissolve the α(hydroxy-keto)retinoic acids may vary somewhat. Ordinarily, the concentration of the solvent in the finished product will be in the range of from 5 to 50% by volume and preferably from 2% to 20% by volume based on the total volume of finished product.

When the therapeutic compositions of this invention take the form of a solution, they are preferably prepared by first dissolving the α(hydroxy-keto)retinoic acids in ethanol or acetone. Water, propylene glycol; 1,3-butanediol, isopropyl myristate or isopropyl palmitate may then be added to the ethanol or acetone solution to complete the composition.

The ratio of the vehicle contained in the compositions of this invention may also vary somewhat. However, in the preferred form of this invention, each vehicle will usually not exceed 95% by volume of the total finished composition.

Therapeutic Regimens

For the treatment of conditions such as dry skin, ichthyosis, palmar and plantar hyperkeratosis, psoriasis, eczema, Darier's disease, or lichen simplex chronicus, therapeutic compositions of this invention in the form of lotions or creams are preferable. Such creams or lotions are applied thinly to involved areas of skin at frequencies of once to four times daily, the frequency selected being that which is most suitable to the user. Continued applications of the therapeutic compositions is associated with restoration of the involved skin toward a state of normal.

For the treatment of acne preferred forms of the therapeutic compositions may be a cream, lotion, solution or alcoholic gel, which are applied usually twice daily to the involved areas. Improvement of acne toward status of normal occurs with continued use of the therapeutic composition and improvement is usually substantial after several weeks of such use.

For the treatment of dandruff, therapeutic composition in the form of a solution, or lotion is preferable. Such solution or lotion is applied to the scalp after shampooing the hair, a procedure repeated once or twice weekly to eradicate symptoms and signs of dandruff, which usually occurs in 1 to 3 weeks.

For the treatment of skin cancer the preferred form of the therapeutic composition may be as a cream, lotion or solution applied to areas of skin in which skin cancers are developing, which is usually discernible by the presence of lesions known as keratoses. With continued applications of such therapeutic compositions twice daily, keratoses can be eradicated and the appearance of new keratoses restrained.

As noted above, compounds III and IV, that is, compounds:

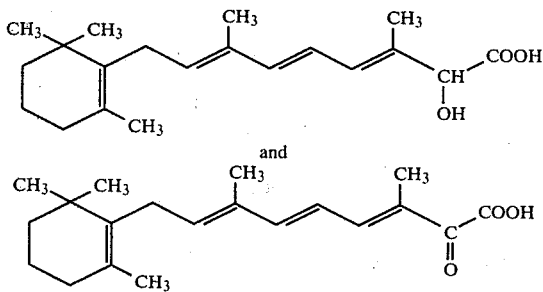

are useful as intermediates in the preparation of the α(hydroxy-keto)retinoic acids. However, these compounds are believed to be biologically active and to have therapeutic properties similar to those exhibited by the α(hydroxy-keto) retinoic acids. These compounds may also be employed in admixture with each other.

The following Examples are given to further illustrate the present invention. It is to be understood, however, that the invention is not limited thereto.

EXAMPLE 1

Synthesis of $C_{19}$ Cyanohydrin (II)

The $C_{19}$ aldehyde (I) 27.2 g (0.1 mole) is dissolved in 400 ml of methanol and acetone cyanohydrin 10.1 ml (0.11 mole) is added to the solution. The mixture is heated to a refluxing for 3 hours according to the method of Julia et al (L. F. Fieser and M. Fieser in Reagents for Organic Synthesis Vol. 1, 5, 1957) after which the mixture is evaporated at 35° C. in a vacuum to give $C_{19}$ cyanohydrin (II).

EXAMPLE 2

Synthesis of Alphahydroxy $C_{20}$ Acid (III)

The $C_{19}$ cyanohydrin (II) 30 g (0.1 mole) is mixed with 43 ml of concentrated hydrochloric acid in a 250 ml round bottom glass flask. The reaction mixture is stirred magnetically at room temperature for 12 hours, after which the mixture is evaporated at 35° C. in a vacuum to remove the excess hydrochloric acid and water. The residue thus obtained is extracted with either benzene or ether according to the method of B. B. Corson et al (Organic Syntheses Collective Volume I p. 336-340, 1941).

(A) Extraction with Benzene: The above mentioned residue which contains a mixture of alphahydroxy $C_{20}$ acid (III) and ammonium chloride is stirred magnetically for 30 minutes with 200 ml of benzene. The benzene solution which contains alphahydroxy $C_{20}$ acid (III) is separated from insoluble ammonium chloride by filtration. The benzene solution is then evaporated at 35° C. in a vacuum to afford alphahydroxy $C_{20}$ acid (III).

(B) Extraction with Ether: Alternatively the above mentioned residue which contains a mixture of alphahydroxy $C_{20}$ acid (III) and ammonium chloride may be shaken 30 minutes with 200 ml of ether. The ether solution which contains alphahydroxy $C_{20}$ acid (III) is separated from insoluble ammonium chloride by filtration. The ether solution is then evaporated at 20° C. in a vacuum to give alphahydroxy $C_{20}$ acid (III).

EXAMPLE 3

Synthesis of Alphaketo $C_{20}$ Acid (IV)

The alphahydroxy $C_{20}$ acid (III) 31.9 g (0.1 mole) as prepared above is dissolved in 200 ml of methylene chloride. Pyridinium chlorochromate 21.6 g (0.1 mole) and sodium acetate 8.2 g (0.1 mole) are added to the mixture. The mixture is stirred magnetically for 2 hours at room temperature according to the method of Corey et al (Tetrahedron Letter 2647, 1975) after which the mixture is filtered. The filtrate which is a methylene chloride solution containing alphaketo $C_{20}$ acid (IV) is evaporated at 20° C. in a vacuum to afford alphaketo $C_{20}$ acid (IV).

Alternatively alphaketo $C_{20}$ acid may be synthesized by the following procedures. Alphahydroxy $C_{20}$ acid (III) 31.9 g (0.1 mole) is dissolved in 500 ml of methanol containing 2% of hydrogen chloride. The mixture is stirred magnetically for 5 hours at room temperature, after which the solution is evaporated at 25° C. in a vacuum to remove the excess methanol and hydrogen chloride. Water, 50 ml is added to the residue and the mixture is extracted with 200 ml of ether. On evaporation of the ether solution, the residual product should be alphahydroxy $C_{20}$ acid methyl ester. The alphahydroxy $C_{20}$ acid methyl ester 33.3 g (0.1 mole) is dissolved in 200 ml of methylene chloride and 21.6 g (0.1 mole) of pyridinium chlorochromate is added to the solution with agitation. The mixture is stirred magnetically for 2 hours at room temperature, after which the mixture is filtered. The filtrate is evaporated at 20° C. in a vacuum to give alphaketo $C_{20}$ acid methyl ester. The alphaketo $C_{20}$ acid methyl ester 33.1 g (0.1 mole) is dissolved in 500 ml of 2-N methanolic potassium hydroxide, and the mixture is heated to a refluxing for 1 hour according to the method of Robeson et al (J. Am. Chem. Soc. 77 4111–4119, 1955). The methanolic solution is then evaporated at 25° C. in a vacuum to about 100 ml in volume, after which 300 ml of water is added to the mixture. The mixture is cooled with icewater bath and 10% sulfuric acid is added until pH 4. The mixture is then extracted with 400 ml of ether. On evaporation of ether alphaketo $C_{20}$ acid (IV) is obtained.

EXAMPLE 4

Synthesis of Alphahydroxy(keto)retinoic Acid (V)

The alphaketo $C_{20}$ acid (IV) 31.7 g (0.1 mole) is dissolved in 300 ml of benzene and 4.6 g (0.033 mole) of phosphorous trichloride is added slowly to the solution. The mixture is stirred magnetically at room temperature for 1 hour according to the method of Huisman et al (Rec. Trav. Chim. 95 977, 1956). The mixture is then slowly poured into 300 g of ice. The benzene layer is separated and evaporated at 35° C. in a vacuum to give an equilibrium mixture of α-hydroxyretinoic acid and α-ketoretinoic acid.

EXAMPLE 5

Alpha-hydroxy(α-keto)retinoic acid composition of Example 4 (0.1 g) is dissolved in 50 ml of ethanol. After all the substance is solubilized, 30 ml of water and 20 ml of propylene glycol is added to the alcoholic solution. The solution thus prepared will consist of 0.1% active ingredient.

EXAMPLE 6

Alpha-hydroxy(α-keto)retinoic acid composition of Example 4 (0.05 g) is dissolved in 40 ml of isopropyl myristate, and the solution admixed with 60 g of water-in-oil ointment prepared from mineral oil, petrolatum, spermaceti and water with a surfactant such as sorbitan sesquioleate. The ingredients of said water-in-oil ointment may be present in 10:10:6:68:6 parts by weight, respectively. The water-in-oil lotion thus prepared will consist of 0.05% active ingredient.

EXAMPLE 7

Alpha-hydroxy(α-keto)retinoic acid composition of Example 4 (0.1 g) is dissolved in 10 ml of acetone, and the solution admixed with 90 g of USP grade hydrophilic ointment to a uniform consistency. The water washable cream thus prepared consists of 0.1% active ingredient.

EXAMPLE 8

Alpha-hydroxy(α-keto)retinoic acid composition of Example 4 (0.1 g) is dissolved in 50 ml of ethanol and the solution admixed with 30 ml of water and 20 ml of propylene glycol. A gelling agent such as hydroxyethylcellulose, hydroxypropylcellulose, or hydroxypropylmethylcellulose, 2 g is added to the mixture with agitation. Continue agitation until a gel is formed. The composition thus formulated consists of 0.1% active ingredient in a gel form.

EXAMPLE 9

Alpha-hydroxy(α-keto)retinoic acid composition of Example 4 (0.05 g) is dissolved in 40 ml of mineral oil, and the solution admixed with 60 g of USP grade white petrolatum to a uniform consistency. The water free ointment thus prepared consists of 0.05% active ingredient.

EXAMPLE 10

Alpha-hydroxy(α-keto)retinoic acid composition of Example 4 (0.1 g) is directly mixed with 100 g of water-in-oil ointment prepared from mineral oil, petrolatum, beeswax, isopropyl myristate, water, sorbital, propylene glycol and magnesium oxide with a surfactant such as sorbitan sesquioleate. The ingredients of said water-in-oil ointment may be present in 10:10:5:5:60:3:5:0.2:2 parts by weight respectively. The water-nonwashable cream thus prepared consists of 0.1% active ingredient.

What is claimed is:

1. The compound of formula:

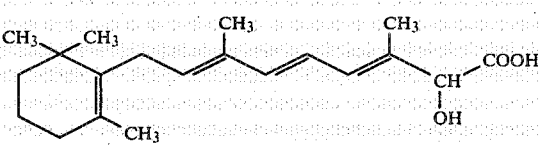

2. The compound of formula:

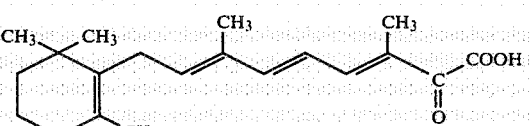

3. A composition for treating the disease symptoms of a disease selected from the group consisting of dry skin, ichthyosis, ance, dandruff, palmar and plantar hyperkeratosis, psoriasis, eczema, mycosis fungoides, Darier's disease, and lichen simplex chronicus comprising:
   a therapeutically effective amount of a material selected from the group consisting of alpha hydroxyretinoic acid, alpha ketoretinoic acid, and mixtures of alpha hydroxyretinoic acid and alpha ketoretinoic acid in a pharmaceutically acceptable carrier for topical application.

4. A composition according to claim 3 wherein said material is α-hydroxyretinoic acid.

5. A composition according to claim 3 wherein said material is α-ketoretinoic acid.

6. A composition according to claim 3 wherein said material is a mixture of α-hydroxyretinoic acid and α-ketoretinoic acid.

7. A composition according to claim 3 including a solvent for said material.

8. A composition according to claim 3 wherein said material comprises from about 0.01 to 2% by weight based on the total weight of the composition.

9. A composition according to claim 8 wherein said material comprises from about 0.02 to 0.5% by weight based on the total weight of the composition.

10. A composition according to claim 8 including from about 5% to 50% by volume based on the volume of the total composition of a solvent for said material.

11. A composition according to claim 10 containing a pharmaceutically acceptable carrier in an amount, exclusive of the amount of said solvent, that does not exceed 95% by volume of the total composition.

12. A composition according to claim 8 in which said solvent comprises from about 2% to 20% by volume based on the volume of the total composition.

13. A composition according to claim 12 containing a pharaceutically acceptable carrier in an amount, exclusive of the amount of said solvent, that does not exceed 95% by volume of the total composition.

14. A method for treating the symptoms of a disease selected from the group consisting of dry skin, ichthyosis, acne, dandruff, palmar and planter hyperkeratosis, psoriasis, eczema, mycosis fungoides, Darier's disease, and lichen simplex chronicus comprising: topically applying to involved areas of the human body a material selected from the group consisting of alpha hydroxyretinoic acid, alpha ketoretinoic acid, and mixtures of alpha hydroxyretinoic acid and alpha ketoretinoic acid in a pharmaceutically acceptable carrier for topical application in an amount sufficient to improve the symptoms of said disease.

* * * * *